United States Patent [19]

Truett

[11] Patent Number: 5,677,191
[45] Date of Patent: Oct. 14, 1997

[54] ORGANIC CHEMICAL COMPOUND TEST PAPERS AND METHOD OF USING SAME

[75] Inventor: William L. Truett, West Brattleboro, Vt.

[73] Assignee: Janos Technology Inc., Townshend, Vt.

[21] Appl. No.: 523,275

[22] Filed: Sep. 5, 1995

[51] Int. Cl.$^6$ ................................................. G01N 21/00
[52] U.S. Cl. .................. 436/166; 436/127; 436/128; 436/129; 436/131; 436/171; 250/339.08; 250/339.12
[58] Field of Search ............................ 436/166, 171, 436/127, 128, 129, 131; 250/339.08, 339.12

[56] References Cited

U.S. PATENT DOCUMENTS

| | | | |
|---|---|---|---|
| 3,915,639 | 10/1975 | Friedenberg | 23/230 B |
| 4,267,234 | 5/1981 | Rembaum | 428/403 |
| 4,369,226 | 1/1983 | Rembaum | 428/334 |
| 4,472,505 | 9/1984 | Manabe et al. | 436/47 |
| 4,752,448 | 6/1988 | Wells et al. | 422/56 |
| 4,840,912 | 6/1989 | Glattstein | 436/92 |
| 4,992,296 | 2/1991 | Gibson | 427/2 |
| 5,482,996 | 1/1996 | Russell et al. | 525/54.1 |
| 5,519,220 | 5/1996 | Truelt | 250/339.08 |

OTHER PUBLICATIONS

Pesek et al. "Synthesis of a Chemically Bonded Weak Cation Exchange Material by Conversion of an Allyl Phase", Chromatographia, vol. 25, No. 11, Nov. 1988, pp. 969–973 Nov. 1988.

Brown et al. "Chemical Defective Work by Computer", Education in Chemistry, (1991), 28(4), 105–6, 111 Jul. 1991.

*Primary Examiner*—Robert J. Warden
*Assistant Examiner*—Sharidan Carrillo
*Attorney, Agent, or Firm*—Herbert M. Wolfson

[57] ABSTRACT

A series of organic test papers are described for the detection and identification of all types of organic compounds such as aldehydes, ketones, esters, acids, amines, isocyanates, anhydrides, amides, nitrides, aromatics, phenols, ethers, and other organic compounds, said test papers comprising an absorbent paper or microporous plastic impregnated with a reagent or reagents capable of reacting with a class of organic compounds. The method of using the test papers for the identification of organic compounds comprises making a presumptive identification of the class of the unknown sample using FTIR spectroscopy, and then placing this presumptively identified sample onto the paper to generate a new substance known as a derivative of the organic compound, which aids in the identification of the unknown organic compound. The test paper containing said sample and reagent is then monitored again using FTIR spectroscopy to observe the reaction and to verify the presumptively identified substance's class identification.

3 Claims, No Drawings

ORGANIC CHEMICAL COMPOUND TEST PAPERS AND METHOD OF USING SAME

BACKGROUND OF THE INVENTION

It is well known that a presumptive identification of a pure organic compound can be made by determining the infrared (IR) spectrum of such a compound and comparing the spectrum with that of thousands of spectra in well established databases which are available from commercial sources.

It is also well known that each organic compound possesses a unique spectrum. However, when structures are very similar, varying by only one or two carbons in a long chain or positional isomers on a ring system the absolute identification may depend upon very minor features in a complex IR spectrum. This method of comparing unknown spectra with a vast database of spectra can be quite costly, requiring computer equipment and software to access the database; furthermore, this method can be imprecise in its examination of very similar structures.

For the past 50 years or more an alternative scheme for a method of absolute identification of organic compounds has been in use. The work upon which this is based is *The Identification of Organic Compounds*, Fuson and Shriner, New York, 1943 and succeeding years. The scheme developed in this work, based in part on previous work by Oliver Kamm, is to subject an unknown organic compound to various simple chemical tests in order to determine the class—such as alcohol, acid, or amine, and then to prepare a derivative by means of reacting the unknown compound with a reagent specific for that class. Further comparisons of melting points and boiling points, and the consultation of tables of data is required for identification.

An example of this method is to determine by simple tests that a compound is presumptively a ketone, and then to prepare a derivative of the ketone via a chemical reaction. Fuson and Shriner list a number of different characteristics for each class of organic compound. It is essential that all of these derivatives possess a crystalline melting point. If a ketone has a boiling range (b.p.), or a melting point (m.p.), this information plus the melting point determination in general gives a proof of identity. Thus with a ketone, with m.p. of 48° C. and the reaction product with 2,4-dinitrophenylhydrazine melting at 238°–239° C. the comparison of these m.p. with elaborate tables in Fuson and Shriner permits identification as benzophenome. In order to be absolutely certain, it is generally mandated that two such derivatives be prepared and their m.p. compared with values in the tables. Thus with benzophenone we can also prepare the semicarbazide derivative, m.p. 161° C. The two determined values, together with the b.p. range, or m.p. constitute identification of the original unknown. These steps toward identification consume a great deal of time, and values are not always in convenient tables for all compounds.

SUMMARY OF THE INVENTION

It is an object of this invention to overcome the aforementioned difficulties in the prior art by utilizing more modern and efficient methods to determine the class of an organic compound and its probable structure, wherein cumbersome data tables are not used.

It is another object of this invention to provide a simple and economical method to determine the class of an organic compound, without requiring the use of costly computer equipment and database software.

It is also an object of this invention to provide a means of verifying the unknown's class identification by means of IR spectral analysis of reactions produced with a known reagent.

The first step in the new method of identification is to determine the IR spectrum of the unknown organic compound using an IR instrument. This is done by placing the liquid or solid sample of the unknown organic compound in the beam of an IR spectrometer. Several types of sampling cells are commercially available for this purpose that will contain a gas, liquid, or solid and position the material in the sample beam of the spectrometer, permitting a spectrum to be determined in seconds.

This spectrum is then examined for its pattern of absorbance bands in order to assign the unknown compound to one of the 20+ classes, such as alcohol, acid, amine, amide, carbonyl, or other class. These rules have been well established over past decades by such authors as L. J. Bellamy in *Infrared Spectra of Complex Molecules*, Wiley, New York, 1955.

When the class of the organic compound is determined it is then possible to readily confirm this assignment. For this purpose our invention employs a small quantity of an appropriate reagent which is placed on a thin sheet of paper or a thin sheet of a microporous plastic. All of the reagents used are solids and are placed on the paper or plastic substrate from solution. When a compound has been assigned to a class, this assignment can be verified by adding the compound under investigation to a reagent on the paper or plastic substrate. In such a case, a reaction will take place and the nature of the outcome will be apparent from a second IR spectrum, that of the reaction product.

An example of this method of identification and verification is given below. An organic compound is examined by IR spectroscopy, and it is determined by the spectral pattern showing strong OH (hydroxyl) vibrations that the substance is an alcohol. The suspect alcohol is added to a sample of phenylisocyanate contained on a substrate of thin paper. The reaction occurs as follows:

The IR spectrum shows a loss of the hydroxyl group vibrations and a new set of vibrations due to the formation of the urethane group, a type of ester. Thus the tentative assignment of the unknown as an alcohol by means of IR spectroscopy, is confirmed by examining the reaction product of the alcohol and phenylisocyanate, which shows a very strong absorbance at 4.5μ, and the course of the reaction can be followed by this band's disappearance. In the event that no reaction occurs, the presumptive identification was in error.

The extension of this simple method to the following classes of organic compounds is described below: alcohols, aldehydes, ketones, acids, amines, isocyanates, anhydrides, alkyl halides, esters, and amides. Use of this method is not limited to these examples but is applicable to all classes of organic compounds.

DETAILED DESCRIPTION OF THE INVENTION

This invention provides a means for the identification and verification of all types of organic compounds using test papers comprising an absorbent paper such as facial tissue or lens cleaning tissue, or microporous plastic such as polyethylene, either type being of thickness 1 mil to 0.1 mil, impregnated with a reagent suitable for reacting with a class of organic compound. According to one embodiment of the present invention there is provided a suitable absorbent paper or microporous plastic impregnated with suitable reagent, with this substrate being in the form of a substrate sample card which fits universally into an FTIR spectrometer sample holder.

The method provided in the invention comprises making a presumptive identification of the class of an unknown compound by analyzing its IR spectrum. After making a presumptive identification of the unknown organic compound via its IR spectrum, said compound is added to the reagent area of the substrate card, said substrate card comprising a solid reagent contained in a 8 mm spot on a thin sheet of paper or microporous plastic which is affixed to a fitted piece of cardboard to be placed in the sample holder of an IR spectrometer. Said substrate card containing the unknown compound is then placed in the sample holder of the spectrometer. The reaction that takes place is monitored over time via a sequence of IR spectra. When the reaction is completed, verification of the class of organic compound is achieved by comparing the resultant spectrum with that of the original unknown compound in the manner described in the following examples:

EXAMPLE 1

Alcohol

A presumed alcohol is reacted with a reagent card labeled "alcohol" which contains maleic anhydride as the reagent. (All reagents are placed on cards by dissolving the reagent in 2 ml of an inert solvent and placing the solvent on the substrate to evaporate. The alcohol reagent is maleic anhydride.)

The alcohol reacts with maleic anhydride very rapidly to yield a new compound, the half-acid ester of maleic acid. The OH group of the alcohol is replaced by the ester group, a strong absorbance at about 1740 $cm^{-1}$. The OH group frequencies at 3333 $cm^{-1}$ and near 1100 $cm^{-1}$ show a progressive disappearance as the alcohol reacts with maleic anhydride.

EXAMPLE 2

Aldehyde

The characteristic aldehyde frequency employed for the recognition of this group is 1725 $cm^{-1}$, together with an absorbance of about 2730 $cm^{-1}$. The reagent employed to confirm this is 2,4-dinitrophenylhydrazine.

The aldehyde bands vanish rapidly and this is quite unique. The product has a minor band near 1666 $cm^{-1}$.

EXAMPLE 3

Ketone

The characteristic ketone frequency is about 1710 $cm^{-1}$ with no other characteristic absorbance. The reagent utilized is the same as for aldehydes, 2,4-dinitrophenylhydrazine.

The strong band at about 1710 $cm^{-1}$ vanishes and a weak band is formed at about 1666 $cm^{-1}$.

EXAMPLE 4

Acid

The characteristic acid bands are at 2500–3000 (broad) with a well defined absorbance at about 1700 $cm^{-1}$. The reagent for acids is sodium bicarbonate which forms the sodium salt of the acid.

The broad band at 2500–3000 $cm^{-1}$ and the band at 1700 $cm^{-1}$ vanish, and a new band occurs near 1666 $cm^{-1}$ due to the acid salt.

EXAMPLE 5

Amine

The characteristic IR bands for amines are two in the region of 3150–3400 $cm^{-1}$ and also at 1600–1625 $cm^{-1}$. The reagent for the amines is phenylisocyanate which forms a urea derivative.

The amine bands are replaced by the urea band near 1740 $cm^{-1}$ and the —NCO band of the reagent at 2270±5 $cm^{-1}$ disappears. The —NCO band is the strongest known infrared absorbance.

EXAMPLE 6

Isocyanates

The characteristic isocyanate band is at 2270±5 $cm^{-1}$ and is very strong. The reagent for this group is decyl alcohol.

The isocyanate band vanishes due to the reaction with the alcohol and a urethane band forms near 1740 $cm^{-1}$.

EXAMPLE 7

Anhydride

The characteristic anhydride bands are twofold, the one at 1800–1825 $cm^{-1}$, and the second at 1740–1770 $cm^{-1}$. The reagent for this group is an alcohol, decyl alcohol.

The anhydride bands are swiftly replaced by a single band due to ester which occurs at 1720–1725 $cm^{-1}$ and masks other bands due to the acid formed.

EXAMPLE 8

Alkyl halides

The characteristic bands for alkyl halides are broadly seen from 1200–700 $cm^{-1}$ and are quite strong. The reagent for this group is silver nitrate.

The reaction gives a well defined precipitate of Silver halide, which does not have an infrared spectrum, but the strong diminution of the alkyl halide peaks is indicative of the presence of alkyl halide.

EXAMPLE 9

Ester

The characteristic ester band is about 1720–1725 $cm^{-1}$ and is quite strong. The reagent for this group is benzylamine, the product is a benzamidE.

The strong ester band rapidly vanishes and two new bands due to amide appear at 1645 and 1680 $cm^{-1}$.

EXAMPLE 10

Amide

The characteristic amide bands are at 1645 and 1680 $cm^{-1}$. The reagent for this group is phenylisocyanate.

The product is a urea derivative and the key band to follow is the disappearance of the —NCO band at 2270 $cm^{-1}$, and the new band due to the product at about 1740 $cm^{-1}$.

Experimental:

The addition of the unknown to the reagent of the card involves placing 0.1 ml (2 drops) of the compound to be identified on the card. The temperature used is ambient. The card is immediately inserted in the FTIR instrument and a series of spectra determined over about 5 minutes. No changes in the spectra indicate that a faulty presumptive identification has been made.

The present invention is not limited to the embodiments and examples explained above. The present invention may include any suitable form of sampling device which is adaptable to the test paper and FTIR spectrometer, other suitable reagents for reacting with unknown organic compounds, or other modifications which may be conceived within the scope of the invention.

What is claimed is:

1. A method for identifying the presence of an unknown organic composition contained in a sample by FTIR (Fourier Transform Infrared) spectroscopy comprising:

a) providing a sample having an unknown organic composition to be identified by FTIR spectroscopy, wherein the unknown organic composition may be an alcohol or a ketone;

b) examining infrared spectra of the sample by FTIR to identify characteristic alcohol and ketone bands;

c) providing a reagent for reacting with the unknown organic composition contained in the sample, wherein said reagent is maleic anhydride, or 2,4-dinitrophenylhydrazine;

d) selecting maleic anhydride if alcohol bands in the infrared spectra of the sample are observed;

e) selecting 2,4-dinitrophenylhydrazine if ketone bands in the infrared spectra of the sample are observed;

f) adding the reagent to a thin paper stock selected from the group consisting of facial tissue, lens cleaning tissue, and microporous polyethylene;

g) adding the sample containing the unknown organic composition to the thin paper stock, wherein the organic composition reacts with said reagent at ambient temperature to produce a chemical reaction; and h) monitoring progress of the chemical reaction by examining infrared spectra by FTIR;

i) identifying the unknown composition as an alcohol if the infrared spectra shows the removal of the characteristic alcohol bands and the appearance of half-ester acid bands during the progress of the chemical reaction; and j) identifying the unknown composition as a ketone if infrared spectra shows the removal of the characteristic ketone bands and appearance of hydrazine bands during the progress of the chemical reaction.

2. A method according to claim 1, wherein the alcohol bands occur at 3333 $cm^{-1}$ and 1100 $cm^{-1}$ and the half-ester acid bands occur at 1710 $cm^{-1}$ and 1810 $cm^{-1}$.

3. A method according to claim 1, wherein the ketone bands occur at 1710 $cm^{-1}$ and the hydrazine bands occur at 1666 $cm^{-1}$.

* * * * *